(12) United States Patent
Lin

(10) Patent No.: US 9,891,171 B2
(45) Date of Patent: Feb. 13, 2018

(54) SENSING MODULE AND SENSING METHOD

(71) Applicant: Personal Genomics, Inc., Grand Cayman (KY)

(72) Inventor: Sheng-Fu Lin, New Taipei (TW)

(73) Assignee: Personal Genomics, Inc., Grand Cayman (KY)

( * ) Notice: Subject to any disclaimer, the term of this patent is extended or adjusted under 35 U.S.C. 154(b) by 0 days.

(21) Appl. No.: 15/220,402

(22) Filed: Jul. 27, 2016

(65) Prior Publication Data

US 2017/0030832 A1 Feb. 2, 2017

Related U.S. Application Data

(60) Provisional application No. 62/197,532, filed on Jul. 27, 2015.

(51) Int. Cl.
*G01N 21/64* (2006.01)
*G01N 21/25* (2006.01)
(Continued)

(52) U.S. Cl.
CPC ......... *G01N 21/645* (2013.01); *G01N 21/253* (2013.01); *G01N 21/648* (2013.01);
(Continued)

(58) Field of Classification Search
CPC ........ G01N 21/17; G01N 21/45; G01N 21/63; G01N 21/64; G01N 21/65; G01N 21/253;
(Continued)

(56) References Cited

U.S. PATENT DOCUMENTS 3,814,498 A * 6/1974 Tomlinson, III ....... G02B 6/124
359/569
5,442,169 A * 8/1995 Kunz ....................... G01D 5/26
250/227.18
(Continued)

FOREIGN PATENT DOCUMENTS

CN 101617211 12/2009
TW 201137341 11/2011
(Continued)

OTHER PUBLICATIONS

"Search Report of European Counterpart Application," dated Jan. 25, 2017, p. 1-p. 10.
(Continued)

*Primary Examiner* — Kiho Kim
(74) *Attorney, Agent, or Firm* — JCIPRNET

(57) ABSTRACT

A sensing module including a sample loading layer, a sensing layer and an optical resonance layer locating between the sample loading layer and the sensing layer is provided. The sample loading layer includes at least a sample loading depression, and the sample loading depression exposes part of the optical resonance layer, and the sample loading depression is adapted to load sample. A surface of the optical resonance layer has optical resonance structures, and the optical resonance structures are located beside bottom of the sample loading depression or below the bottom of the sample loading depression. The sensing layer is configured to receive light and turn it into electrical signals. A sensing method is also provided.

35 Claims, 3 Drawing Sheets

(51) Int. Cl.
*G01N 33/543* (2006.01)
*G01N 33/52* (2006.01)

(52) U.S. Cl.
CPC ..... *G01N 21/6428* (2013.01); *G01N 21/6452* (2013.01); *G01N 21/6454* (2013.01); *G01N 33/525* (2013.01); *G01N 33/54373* (2013.01)

(58) Field of Classification Search
CPC ............. G01N 21/774; G01N 21/7743; G01N 2021/0112; G02B 2006/1213; G01D 5/26
See application file for complete search history.

(56) References Cited

U.S. PATENT DOCUMENTS

| | | | |
|---|---|---|---|
| 5,455,178 A * | 10/1995 | Fattinger | G01N 21/7743 385/12 |
| 6,990,259 B2 | 1/2006 | Cunningham | |
| 7,531,786 B2 * | 5/2009 | Cunningham | B01L 3/5085 250/214.1 |
| 7,756,365 B2 | 7/2010 | Cunningham et al. | |
| 7,790,406 B2 | 9/2010 | Cunningham et al. | |
| 7,858,921 B2 | 12/2010 | Stanton et al. | |
| 7,923,239 B2 | 4/2011 | Cunningham et al. | |
| 8,111,401 B2 | 2/2012 | Magnusson et al. | |
| 8,344,333 B2 | 1/2013 | Lu et al. | |
| 8,514,391 B2 | 8/2013 | Wawro et al. | |
| 2005/0012993 A1 * | 1/2005 | Araya | G02B 21/06 359/385 |
| 2005/0110989 A1 | 5/2005 | Schermer et al. | |
| 2006/0273245 A1 | 12/2006 | Kim et al. | |
| 2007/0224264 A1 * | 9/2007 | Antipov | A61K 9/0009 424/463 |
| 2008/0219615 A1 | 9/2008 | Cunningham | |
| 2010/0256918 A1 * | 10/2010 | Chen | C12Q 1/6869 702/19 |
| 2010/0320363 A1 | 12/2010 | Schleipen | |
| 2011/0306143 A1 | 12/2011 | Chiou et al. | |
| 2013/0169960 A1 | 7/2013 | Cunningham | |
| 2014/0367589 A1 | 12/2014 | Chiou et al. | |
| 2015/0141267 A1 * | 5/2015 | Rothberg | C12Q 1/6869 506/2 |

FOREIGN PATENT DOCUMENTS

| | | | |
|---|---|---|---|
| WO | WO 9503538 A1 * | 2/1995 | ............ B01L 3/5085 |
| WO | 2011103507 | 8/2011 | |
| WO | 2014031157 | 2/2014 | |

OTHER PUBLICATIONS

"Office Action of Taiwan Counterpart Application," dated Oct. 18, 2017, p. 1-p. 6.

* cited by examiner

SENSING MODULE AND SENSING METHOD

CROSS REFERENCE TO RELATED APPLICATION

This application claims the priority benefit of U.S. provisional application Ser. No. 62/197,532, filed on Jul. 27, 2015. The entirety of the above-mentioned patent application is hereby incorporated by reference herein and made a part of specification.

BACKGROUND OF THE INVENTION

1. Field of the Invention

The present invention generally relates to a sensing module and a sensing method, in particular, to a sensing module and a sensing method using optical resonance structures and being adapted to sense a single molecule.

2. Description of Related Art

Fluorescence is one of the most sensitive detection and imaging tools available for determining the presence and concentration of analytes in a wide range of applications including DNA sequencing and DNA microarrays. The ability to detect weak signals is essential for assays requiring the detection of analytes at low concentration. To address this challenge, researchers have developed many methods to enhance fluorescence emission and remove the unwanted emission, thereby improving detection sensitivity and signal-to-noise ratio (SNR).

A variety of optical electric sensor (OES) using fluorescence detection techniques have been studied for the purpose of enhancing fluorescence signal and noise reduction. For the purpose of filtering the noise, the filter between the sensor and the analytes need to be constructed with sufficient thickness, so as to provide a proper filter function. However, while the distance between the analytes and the sensor is increased by the filter, the amount of fluorescence being detected by the sensor is also reduced, and therefore the detection sensitivity of the OES is reduced. On the contrary, if the thickness of the filter is reduced so as to improve the sensitivity, the SNR of the OES will also be reduced.

SUMMARY OF THE INVENTION

The present invention is directed to an optical electric sensing module having an optical resonance layer.

The present invention also provides a sensing method of the sensing module with high sensitivity, high SNR, and prevention of photo-bleaching.

In the present invention, a sensing module including a sample loading layer, a sensing layer and an optical resonance layer locating between the sample loading layer and the sensing layer is provided. The sample loading layer includes at least a sample loading depression exposing part of the optical resonance layer, and the sample loading depression is adapted to load sample. A surface of the optical resonance layer has optical resonance structures, and the optical resonance structures are located beside bottom of the sample loading depression or below the bottom of the sample loading depression. The sensing layer is configured to receive light and turn it into electrical signals.

In the present application, a sensing method is provided, including providing the sensing module described above; loading sample into the sample loading region of the sensing module; and illuminating the optical resonance structures with an excitation light, which is a pulse laser.

In the present application, a sensing method is provided, including providing the sensing module described above; loading sample into the sample loading region of the sensing module; and illuminating the optical resonance structures with a plurality of excitation lights. Besides from using an incident light of a certain wavelength that can induce fluorescence of the target ingredient in the sample, the sensing method uses the incident lights to illuminate the optical resonance structures, and the resonant lights on the optical resonance structures excite the sample.

In an embodiment of the present invention, the sample loading depression comprises at least a sample loading well.

In an embodiment of the present invention, the sample loading depression comprises at least a sample loading channel, and the samples forms a fluid in the sample loading channel.

In an embodiment of the present invention, the sensing module further comprises at least a blocking layer disposing above the sample loading channel.

In an embodiment of the present invention, the sensing layer comprises at least a sensing unit, and the sensing unit is disposed below the sample loading depression.

In an embodiment of the present invention, the sensing unit is a semiconductor device of a multi-junction photodiode.

In an embodiment of the present invention, the optical resonance structures are 1-dimensional periodic grating structures or 2-dimensional periodic grating structures.

In an embodiment of the present invention, the sensing module further comprises at least a light source, the light source emits excitation light and illuminates the sample loading depression and the optical resonance structures.

In an embodiment of the present invention, the wavelength of the excitation light falls in a range from 480 nm to 540 nm.

In an embodiment of the present invention, the light source is a laser and the excitation light strikes the optical resonance structures at a resonance angle.

In an embodiment of the present invention, the sensing module satisfies:

$$\lambda/n_{wg} \leq \Lambda \leq \lambda,$$

wherein $\lambda$ is the wavelength of the excitation light in the optical resonance layer, $n_{wg}$ is the refractive index of the optical resonance layer, and $\Lambda$ is the period of the optical resonance structure.

In an embodiment of the present invention, the excitation light excites waveguide-mode resonance at the optical resonance structures.

In an embodiment of the present invention, the sensing module satisfies:

$$d \leq 0.7h,$$

wherein d is depth (or height) of every optical resonance structures, and h is total thickness of the optical resonance layer.

In an embodiment of the present invention, the sensing module further comprises a substrate disposing between the sensing layer and the optical resonance layer. The sensing module satisfies:

$$n_{wg} > n_{substrate} \geq n_{top};$$

$n_{wg}$ is the refractive index of the optical resonance layer, and $n_{substrate}$ is the refractive index of the substrate or adjacent layer, and $n_{top}$ is the refractive index of the sample loading layer.

In an embodiment of the present invention, the surface having the optical resonance structures faces the sample loading layer.

In an embodiment of the present invention, emission wavelength of the sample near the optical resonance structures is shorter than wavelength of the excitation light.

In an embodiment of the present invention, the wavelength of the excitation light falls in a range from 800 nm to 1100 nm.

By depositing the optical resonance layer between the sample loading layer and the sensing layer, the sensing module of this invention, is formed. The sensing module has the characteristics of high sensitivity, and high SNR. Furthermore, the sensing method using the sensing module can analyze sample and preventing the photo-bleach of the sample, and therefore provides a high sensitivity and high SNR sensing function.

In order to make the above and other features and advantages of the present invention more comprehensible, embodiments accompanied with figures are described in details below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
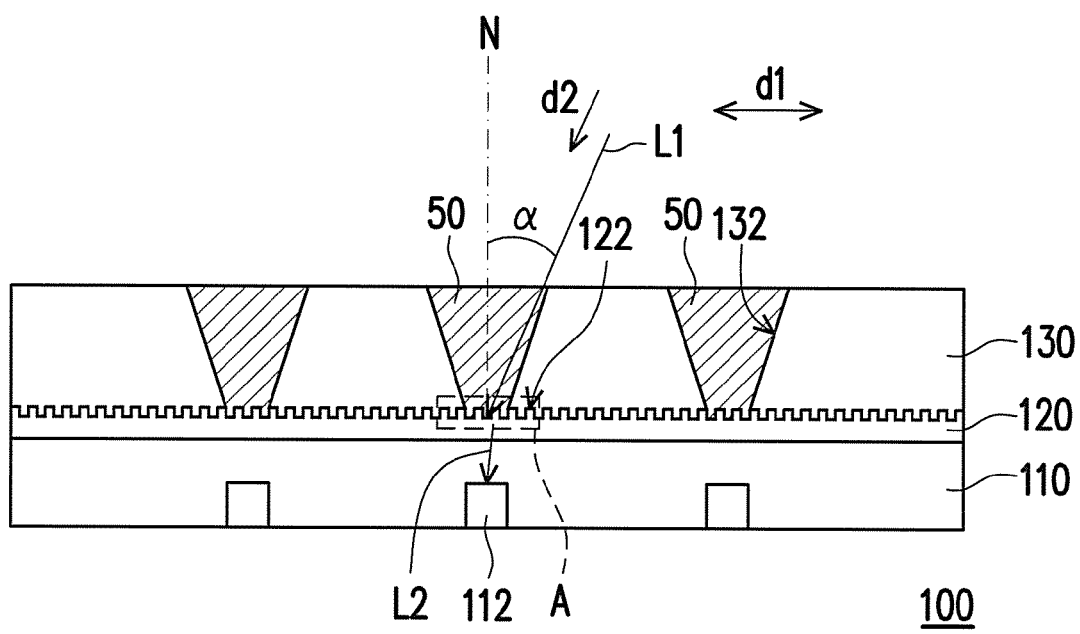
FIG. 1 is a schematic cross-sectional view of the sensing module of the first embodiment.

Reference will now be made in detail to the present preferred embodiments of the invention, examples of which are illustrated in the accompanying drawings. Wherever possible, the same reference numbers are used in the drawings and the description to refer to the same or like parts.

First Embodiment

In the first embodiment of this invention, a sensing module is adapted to analyze a sample and generate signals with good signal-noise ratio (SNR).

FIG. 1 is a schematic cross-sectional view of the sensing module of the first embodiment. In the first embodiment of this invention, the sensing module 100 includes a sample loading layer 130, a sensing layer 110 and an optical resonance layer 120 locating between the sample loading layer 130 and the sensing layer 110. The sample loading layer 130 has at least a sample loading depression, and the sample loading depression of this embodiment includes sample loading wells 132. The sample loading wells 132 exposing parts of the optical resonance layer 120 are adapted to load samples 50. A surface of the optical resonance layer 120 has optical resonance structures 122, and the optical resonance structures 122 are located beside the bottoms of the sample loading wells 132 or below the bottoms of the sample loading wells 132. The sensing layer 110 is adapted to receive light and turn it into electrical signals.

In this embodiment, an incident light L1 having a specific wavelength is adapted to resonate in the optical resonance structures 122. The optical resonance structures 122 are configured to resonate a light when the light having the specific wavelength is illuminating the optical resonance structures 122 at a resonance angle α, and the optical resonance layer 120 is configured to guide part of the light coupled in the optical resonance layer 120 in a direction d1. After the incident light L1 illuminated the optical resonance structures 122 at the incident angle α, the incident light L1 is coupled into the optical resonance layer 120. In other words, the optical resonance layer 120 with the optical resonance structures 122 provides an incident light filtering function between the sample 50 and the sensing layer 110, so the incident light L1 transmitting along direction d2 couldn't transmit to the sensing layer 110, and a resonance mode (or guided mode, leaky mode, waveguide mode) of the optical resonance structures 122 of the optical resonance layer 120 is generated, so the intensity of the incident light L1 in region A is enhanced by the resonance.

In the embodiment, the optical resonance structures 122 are 1-dimensional periodic grating structures, and the optical resonance structures 122 are arranged along direction d1, but the invention is not limited thereto. In other embodiment of the invention, the optical resonance structures of the sensing module is a 2-dimensional periodic grating structures.

The sensing module 100 of the first embodiment further includes a light source providing the excitation light, which is the incident light L1 of this embodiment. The incident light L1 is adapted to make at least one target ingredient in the sample 50 to fluoresce. The fluorescence of the target ingredient is caused by the absorption of radiation at the wavelength of the incident light L1 followed by nearly immediate re-radiation at a different wavelength, which is able to transmit through the optical resonance layer 120.

To be more specific, the wavelength of the excitation light, which is the incident light L1, falls in a range from 480 nm to 540 nm, and the sensing module 100 satisfies: $\lambda/n_{wg} \leq \Lambda \leq \lambda$, wherein $\lambda$ is the wavelength of the incident light L1 in the optical resonance layer 120, $n_{wg}$ is the refractive index of the optical resonance layer 120, and $\Lambda$ is the distance from the centre of one of the optical resonance structures 122 to the centre of the adjacent optical resonance structure 122. In other words, $\Lambda$ is the period of the optical resonance structures 122. For example, while the wavelength of the incident light L1 is 532 nm and the refractive index $n_{wg}$ of the optical resonance layer 120 is 2, the period $\Lambda$ in the optical resonance layer 120 falls in the range from 266 nm to 532 nm.

On the other hand, the optical resonance structures 122 of the embodiment is facing the sample loading layer 130, and the optical resonance structures 122 of the sensing module 100 of the embodiment satisfies: $d \leq 0.7h$, wherein d is depth (or height) of every optical resonance structures 122, and h is total thickness of the optical resonance layer 120 to the bottom of the optical resonance layer 120. Therefore, for a 150 nm optical resonance layer the depth of resonance structure is smaller than 105 nm.

In the sensing module 100 of the embodiment, the refractive index of the optical resonance layer 120 is higher than the refractive index of the sample loading layer 130, and the refractive index of the optical resonance layer 120 is also higher than the refractive index of the material between the optical resonance layer 120 and the sensing layer 110. In other words, the sensing module 100 of the embodiment can further include a substrate locating between the optical resonance layer 120 and the sensing layer 110, and the sensing module 100 satisfies $n_{wg} > n_{substrate} \geq n_{top}$, wherein $n_{wg}$ is the refractive index of the optical resonance layer 120, and $n_{substrate}$ is the refractive index of the substrate located between the optical resonance layer 120 and the sensing layer 110, and $n_{top}$ is the refractive index of the sample loading layer 130. Therefore, the waveguide resonance mode of the optical resonance layer 120 can be excited by the excitation light L1.

The sensing layer 110 includes sensing units 112 being adapted to receive light and turn it into electrical signals, and the sensing units 112 are disposed below the sample loading wells 132. In detail, the sensing units 112 are configured to receive the fluorescence L2 of the target ingredient, so as to generate an analysis of the samples 50. In more details, the incident light L1 strikes on the optical resonance structures 122 of the optical resonance layer 120, and the resonance mode of at least one optical resonance structures 122 is generated. The incident light L1 coupled in the optical resonance layer 120 excites the samples 50 near the bottom of the sample loading wells 132, and the target ingredient in the samples 50 emits the fluorescence. The sensing units 112 receive the fluorescence L2, and generating an electrical fluorescence signal related to the samples 50 in the sample loading wells 132. The sensing units 112 in this embodiment is a multi-junction photodiode, wherein the multi-junction photodiode is configured to receive lights of multiple wavelengths and generate multiple signals according to each intensity of lights, while the invention is not limited to the variety of the sensing unit. In other embodiments of the invention, the sensing unit of the sensing module is a semiconductor device of a single junction photodiode.

Since, in the sensing module of the first embodiment, the incident light L1 is coupled in the optical resonance layer 120, and only the fluorescence L2 of the sample 50 can reach the sensing units 112, the optical resonance layer 120 provides a good incident light filtering function between the sample 50 and the sensing units 112. Also, the resonance mode of the optical resonance layer 120 can increase the intensity of the excitation to the sample 50 near the bottom of the sample loading well 132. Therefore, the sensing units 112 can generate electrical signals with high SNR.

The target ingredient of the sample 50 mentioned above includes, for example, dye intercalated into plasmids, DNAs, nucleotides, proteins, glucose or any other sample 50 inserted by matters that can fluoresce when an incident light is sticking thereon, while the invention is not limited to the variety of the target ingredients.

The optical resonance structures 122 include gratings arranged in a direction d1, and the incident light L1 is, for example, a TM (transverse magnetic) or TE (transverse electric) polarized light. Therefore, with the specific incident angle, the incident light L1 can generate the resonance mode of optical resonance layer 120. The resonance mode not only can prevent the sensing units 112 from being radiate by the incident light L1, but also enhanced the intensity of the radiation of the sample in the bottom of the sample loading wells 132. In other words, the optical resonance layer 120, in particular, combines the function of a filter and an optical enhancing structure, so thickness of the sensing module 100 can be reduced, and the SNR of the signal can be improved.

Sample loading layers and optical resonance layers in embodiments of the invention are not limited to the sample loading layer 130 and the optical resonance layer 120. In other embodiment of the invention, every sample loading wells has bottom being adjacent to optical resonance structures of optical resonance layer, and the incident light is able to transmit through the bottoms and illuminate the optical resonance structures of the optical resonance layer, while the invention is not limited to the variety of sample loading wells.

Second Embodiment

In the second embodiment of this invention, a sensing module assay a sample or an analytic and generate signals with better signal-noise ratio (SNR), and the sample can remain nearly the same condition after the assay.

Figure 2A:
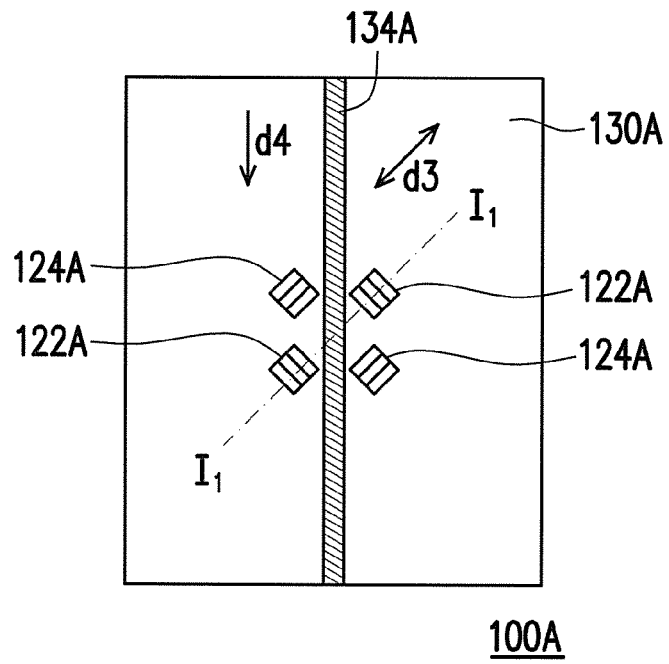
FIG. 2A is a schematic top view of the sensing module of the second embodiment.
Figure 2B:
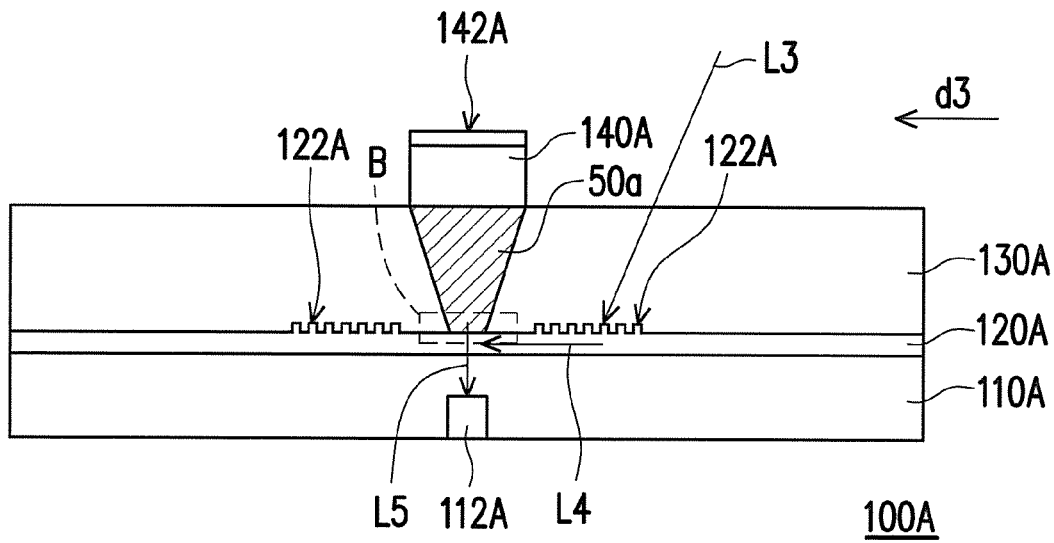
FIG. 2B is a schematic cross-sectional view of the sensing module according to the line I1 in FIG. 2A.

FIG. 2A is a schematic top view of the sensing module of the second embodiment. FIG. 2B is a schematic cross-sectional view of the sensing module according to the line I1 in FIG. 2A. In the second embodiment of the invention, the sensing module 100A includes a sample loading layer 130A, a sensing layer 110A and an optical resonance layer 120A locating between the sample loading layer 130A and the sensing layer 110A, and the sample loading layer 130A include a sample loading depression, and the sample loading depression of the embodiment include sample loading channel 134A, and the sensing layer 110A includes sensing unit 112A being adapted to receive light and turn it into electrical signals.

The sample 50A forms a fluid in the sample loading channel 134A. In this embodiment, samples are flowing through the sample loading channel 134A in a direction d4, and the sensing module 100A further includes a blocking layer 140A locating above the sample loading channel 134A, wherein the blocking layer 140A has an optical blocking surface 142A being adapted to block the incident excitation light L3. Therefore, the samples 50A in the sample loading well 134A won't be directly exposed under the radiation of the incident excitation light L3.

Pairs of optical resonance structures 122A, 124A are located beside the bottom of the sample loading channel 134A in this embodiment. The optical guiding resonance layer 120A includes pairs of optical resonance structures 122A, 124A, and part of the sample loading channel 134A is located between each pair of the optical resonance structures 122A, 124A. The optical resonance structures 122A are arranged in a direction d3, and the optical resonance structures 124A are arranged in another direction perpendicular to direction d3, and region B of the bottom of the sample loading channel 134A is located between the optical resonance structures 122A.

When the incident light L3 strikes the resonance structures 122A, for example, at an incident resonance angle. The resonance mode of the optical resonance structures 122A is generated, and part of the excitation light L3 coupled in the optical resonance layer 120A is guided along direction d3. The sample 50A in the region B of the bottom of the sample loading channel 134A is excite by the guided excitation light L4, and target ingredient in the sample 50A fluoresce under the excitation of the guided excitation light L4. The sensing unit 112A can receive the fluorescence from the sample 50A, and generating an electrical fluorescence signal related to the sample 50A in the region B. In this embodiment, one of the optical resonance structures 122A, 124A is illuminated by a TM polarized light, and the other one is illuminated by a TE (transverse electric) polarized light, and the excitation light L3 includes the TM polarized light and the TE polarized light.

In this embodiment, since the resonance mode of the optical resonance structures 122A, 124A can all be generated by the excitation light L3, therefore the amount of excitation light L3 coupled in the optical guiding resonance layer is increased, and the samples 50A in the region B can be radiated with the guided excitation light L4 from optical resonance structures 122A, 124A, and the intensity of the guided excitation light L4 in the region B is sufficient. Also, the blocking layer 140A can keep the samples 50A from direct radiation of the excitation light L3, so the condition of all the samples 50A won't be affect by the excitation light L3. In other words, since the sensing module 100A not only can prevent the sensing unit 112A from striking by the excitation light L3, but also can prevent the sample 50A from directly striking by the incident light L3, optical effects such as photo-bleaching of the samples 50A can be prevent, and the quality such as SNR of the signal can be improved at the same time.

In other embodiment, by using an excitation light L3 that can directly illuminate the resonance structures 122A, 124A without illuminating the sample loading channel 134A, there can be no blocking layer above the sample loading channel 134A, while the invention is not limited to the variety of sample loading channels.

Third Embodiment

In the third embodiment of this invention, a sensing method using the sensing module 100 or 100A can prevent the sample from optical effects such as photo-bleaching. Referring in FIG. 1, the sensing method of this embodiment can apply on the sensing module 100, for example. Besides from using continuous wave as an excitation light L1, the sensing method uses pulsed laser to illuminate the sample 50 and the optical resonance structure 122.

Using pulsed laser as the excitation light L1 can reduce the duration of exposing sample 50 to the excitation light L1, and the effect on the condition of the sample 50 can be reduced. Because the excitation light L1 is adapted to generate the resonance mode of the optical resonance structures 122, resonance of the excitation light L1 can compensate the intensity of incident light in region A, and the intensity of the excitation light L1 in the region A won't be reduced by the reduction of the duration of radiation. In other words, the sensing method in this embodiment can analyze the sample 50 by striking pulsed laser on the optical resonance layer. Without the continuous radiation of the incident light L1, the optical effects in the samples 50 can be reduced.

Fourth Embodiment

Figure 3:
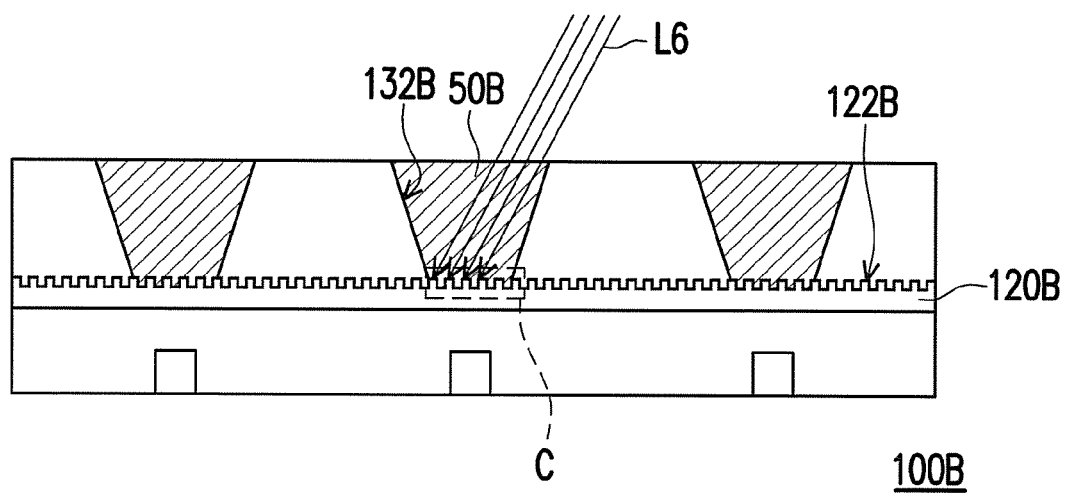
FIG. 3 is a schematic cross-sectional view of the sensing module of the fourth embodiment.

FIG. 3 is a schematic cross-sectional view of the sensing module of the fourth embodiment. In the fourth embodiment of this invention, a sensing method using the sensing module above can prevent the sample from optical effects such as photo-bleaching. Referring in FIG. 3, the sensing method of this embodiment can apply on the sensing module 100B, for example, and the sensing method can also apply on the sensing module 100, 100A above. Besides from using an excitation light L1 of a certain wavelength that can induce fluorescence of the target ingredient in the sample 50B, the sensing method uses an excitation light L6 of longer wavelength striking the sample 50B and the optical resonance structure 122B.

To be more specific, the wavelength of the excitation light L6 is double of the excitation wavelength of the target ingredient in the sample 50B, and resonance mode of optical resonance structures 122B of optical resonance layer 120B is configured to resonant by the excitation light L6. Also, the emission wavelength of the target ingredient in the sample 50B is shorter than wavelength of the excitation light L6.

With high intensity of radiation of excitation light L6 in region C of the bottom of the sample loading well 132B and further enhancement of the intensity by the resonance of excitation light L6 in the optical resonance structures 122B, two-photo absorption condition can be achieved on the target ingredient in the samples 50B. Therefore, the samples 50B outside the region C is illuminated by incident light L6 of longer wavelength, and optical effects such as photo-bleaching can be prevented.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

In summary, the sensing module of the embodiment includes an optical resonance layer having optical resonance structures, and resonance mode of the optical resonance structures are adapted to be excited by an excitation light, and therefore the optical intensity around the optical resonance structures is increased, so as to illuminate sample at bottom of the sample loading depression of the sample loading layer. Since the optical intensity of the excitation light can be increased by the resonance mode of the optical resonance structures, and the excitation light can be filtered before the sensing layer, the fluorescence of the sample can also be increased after being illuminated by the excitation light, and the sensitivity and the SNR of the sensing module can also be improved. The sensing method of the embodiment can be apply to the sensing module mention above, and the excitation light of the sensing method can prevent photo-bleaching of the sample. Therefore, the sensing method can provided a high sensitivity, SNR and good sample protection.

What is claimed is:

1. A sensing module comprising:
    a sample loading layer comprising at least a sample loading depression;
    a sensing layer being configured to receive light and turn it into electrical signals;
    an optical resonance layer locating between the sample loading layer and the sensing layer, wherein the sample loading depression exposing part of the optical resonance layer are adapted to load samples, and a surface of the optical resonance layer has optical resonance structures, and the optical resonance structures are located beside bottom of the sample loading depression or at the bottom of the sample loading depression; and
    at least a light source, configured to provide an excitation light to the optical resonance layer through the sample loading layer, wherein the excitation light has a wavelength in the optical resonance layer and the wavelength is not shorter than the period of the optical resonance structure.

2. The sensing module according to claim 1, wherein the sample loading depression comprises at least a sample loading well.

3. The sensing module according to claim 1, wherein the sample loading depression comprises at least a sample loading channel, and the samples forms a fluid in the sample loading channel.

4. The sensing module according to claim 3 further comprising:

at least a blocking layer disposing above the sample loading channel.

5. The sensing module according to claim 1, wherein the sensing layer comprises at least a sensing unit, and the sensing unit is disposed below the sample loading depression.

6. The sensing module according to claim 1, wherein the sensing unit is a semiconductor device of a multi-junction photodiode.

7. The sensing module according to claim 1, wherein the optical resonance structures are 1-dimensional periodic grating structures or 2-dimensional periodic grating structures.

8. The sensing module according to claim 1, wherein the light source illuminates the sample loading depression and the optical resonance structures.

9. The sensing module according to claim 8, wherein the light source is a laser and the excitation light strikes the optical resonance structures at a resonance angle.

10. The sensing module according to claim 8 satisfying:

$$\lambda/n_{wg} \leq \Lambda \leq \lambda,$$

wherein $\lambda$ is the wavelength of the excitation light in the optical resonance layer, $n_{wg}$ is the refractive index of the optical resonance layer, and $\Lambda$ is the period of optical resonance structure.

11. The sensing module according to claim 8, wherein the excitation light excites waveguide-mode resonance in the optical resonance structures.

12. The sensing module according to claim 1 satisfying:

$$d \leq 0.7h,$$

wherein d is depth of every optical resonance structures, and his total height of the optical resonance layer.

13. The sensing module according to claim 1 further comprising:
a substrate disposing between the sensing layer and the optical resonance layer, wherein the sensing module satisfies:

$$n_{wg} > n_{substrate} \geq n_{top};$$

$n_{wg}$ is the refractive index of the optical resonance layer, and $n_{substrate}$ is the refractive index of the substrate, and $n_{top}$ is the refractive index of the sample loading layer.

14. The sensing module according to claim 1, wherein the surface having the optical resonance structures faces the sample loading layer.

15. A sensing method, applicable to a sensing module comprising a sample loading layer, a sensing layer, and an optical resonance layer located between the sample loading layer and the sensing layer, the sensing method comprising:
receiving an excitation light, wherein the excitation light being a pulse laser is projected onto optical resonance structures of the optical resonance layer through the sample loading layer;
blocking the excitation light from transmitted to the sensing layer by the optical resonance layer, and coupling the excitation light into the optical resonance layer by the optical resonance structures of the optical resonance layer;
exciting sample loaded in the sample loading layer by the excitation light coupled into the optical resonance layer, to generate a fluorescence; and
receiving the fluorescence and transforming the fluorescence into a plurality of electrical signals by the sensing layer.

16. The sensing method according to claim 15, wherein the excitation light strikes the optical resonance structures at a resonance angle.

17. The sensing method according to claim 15, wherein the excitation light is configured to excite a waveguide-mode resonance in the optical resonance structures.

18. The sensing method according to claim 15, wherein the optical resonance structures are 1-dimensional periodic grating structures or 2-dimensional periodic grating structures.

19. The sensing method according to claim 15, wherein the sample loading layer comprises at least a sample loading depression, wherein the sensing layer comprises at least a sensing unit, and the sensing unit is disposed below the sample loading depression.

20. The sensing method according to claim 19, wherein the sensing unit is a semiconductor device of a multi-junction photodiode.

21. The sensing method according to claim 15, wherein the sensing module satisfies:

$$\lambda/n_{wg} \leq \Lambda \leq \lambda,$$

wherein $\lambda$ is the wavelength of the excitation light in the optical resonance layer, $n_{wg}$ is the refractive index of the optical resonance layer, and $\Lambda$ is the period of optical resonance structure.

22. The sensing method according to claim 15, wherein the sensing module satisfies:

$$d \leq 0.7h,$$

wherein d is depth of every optical resonance structures, and his total height of the optical resonance layer.

23. The sensing method according to claim 15, wherein the sensing module further comprises:
a substrate disposing between the sensing layer and the optical resonance layer, wherein the sensing module satisfies:

$$n_{wg} > n_{substrate} \geq n_{top};$$

$n_{wg}$ is the refractive index of the optical resonance layer, and $n_{substrate}$ is the refractive index of the substrate, and $n_{top}$ is the refractive index of the sample loading layer.

24. The sensing method according to claim 15, wherein the surface having the optical resonance structures faces the sample loading layer.

25. A sensing method applicable to a sensing module comprising a sample loading layer, a sensing layer, and an optical resonance layer located between the sample loading layer and the sensing layer, the sensing method comprising:
receiving a plurality of excitation light, wherein the excitation lights are projected onto optical resonance structures of the optical resonance layer through the sample loading layer, and the excitation lights overlap on the optical resonance structures,
blocking the excitation lights from transmitted to the sensing layer by the optical resonance layer, and coupling the excitation lights into the optical resonance layer by the optical resonance structures of the optical resonance layer;
exciting sample loaded in the sample loading layer by the excitation lights coupled into the optical resonance layer, to generate a fluorescence; and
receiving the fluorescence and transforming the fluorescence into a plurality of electrical signals by the sensing layer.

26. The sensing method according to claim 25, wherein the excitation light strikes the optical resonance structures at a resonance angle.

27. The sensing method according to claim 25, wherein the excitation light is configured to excite a waveguide-mode resonance at the optical resonance structures.

28. The sensing method according to claim 27, wherein wavelength of the fluorescence near the optical resonance structures is shorter than wavelength of the excitation light.

29. The sensing method according to claim 25, wherein the optical resonance structures are 1-dimensional periodic grating structures or 2-dimensional periodic grating structures.

30. The sensing method according to claim 25, wherein the sample loading layer comprises at least a sample loading depression, wherein the sensing layer comprises at least a sensing unit, and the sensing unit is disposed below the sample loading depression.

31. The sensing method according to claim 30, wherein the sensing unit s a semiconductor device of a multi-junction photodiode.

32. The sensing method according to claim 25, wherein the sensing module satisfies:

$$\lambda/n_{wg} \leq \Lambda \leq \lambda,$$

wherein $\lambda$ is the wavelength of the excitation light in the optical resonance layer, $n_{wg}$ is the refractive index of the optical resonance layer, and $\Lambda$ is the period of optical resonance structure.

33. The sensing method according to claim 25, wherein the sensing module satisfies:

$$d \leq 0.7h,$$

wherein d is depth of every optical resonance structures, and h is total of the optical resonance layer.

34. The sensing method according to claim 25, wherein the sensing module further comprises:

a substrate disposing between the sensing layer and the optical resonance layer, wherein the sensing module satisfies:

$$n_{wg} > n_{substrate} \geq n_{top};$$

$n_{wg}$ is the refractive index of the optical resonance layer, and $n_{substrate}$ is the refractive index of the substrate, and $n_{top}$ is the refractive index of the sample loading layer.

35. The sensing method according to claim 25, wherein the surface having the optical resonance structures faces the sample loading layer.

* * * * *